United States Patent
Luan

(10) Patent No.: US 10,612,008 B2
(45) Date of Patent: Apr. 7, 2020

(54) STREPTOMYCES SP. STRAIN AND METHOD FOR PREPARING SULFIDE OXIDASE PREPARATION FROM THE SAME

(71) Applicant: QINGDAO YAODONG GROUP, Qingdao (CN)

(72) Inventor: Xingshe Luan, Qingdao (CN)

(73) Assignee: QINGDAO YAODONG GROUP, Shandong (CN)

( * ) Notice: Subject to any disclaimer, the term of this patent is extended or adjusted under 35 U.S.C. 154(b) by 387 days.

(21) Appl. No.: 15/360,881

(22) Filed: Nov. 23, 2016

(65) Prior Publication Data

US 2018/0057799 A1 Mar. 1, 2018

(30) Foreign Application Priority Data

Aug. 26, 2016 (CN) .......................... 2016 1 0739207

(51) Int. Cl.
  *C12N 9/02* (2006.01)
  *C12N 1/20* (2006.01)
  *C12P 21/02* (2006.01)
  *C12R 1/465* (2006.01)

(52) U.S. Cl.
  CPC .............. *C12N 9/0051* (2013.01); *C12N 1/20* (2013.01); *C12P 21/02* (2013.01); *C12R 1/465* (2013.01); *C12Y 108/03001* (2013.01)

(58) Field of Classification Search
  CPC ......... C12N 1/20; C12N 9/0051; C12P 21/02; C12R 1/465; C12Y 108/03001
  See application file for complete search history.

(56) References Cited

FOREIGN PATENT DOCUMENTS

CN 101565693 A 10/2009
CN 104694423 A 6/2015

OTHER PUBLICATIONS

Ohta et al. (1997) Purification and properties of a sulfide-oxidizing enzyme from *Streptomyces* sp. strain SH91. Canadian Journal of Microbiology 43(12): 1097-1101. (Year: 1997).*

Sun, Qi, "Sutdy on Mutation Breeding and Optimization of Fermentation Conditions of *Streptomyces thermocarbonxydus* var *shandaensis*" Chinese Doctoral Dissertations & Master's Theses Full-text Database Engineering Science and Technology I , vol. 8, Shandong University Master's Thesis, (Dec. 15, 2005), pp. 1-16.

The Chinese First Examination Report of corresponding Chinese application No. 201610739207.X, dated Jan. 22, 2019.

* cited by examiner

*Primary Examiner* — Lisa J Hobbs
(74) *Attorney, Agent, or Firm* — J.C. Patents

(57) ABSTRACT

The present invention discloses a *Streptomyces* sp. strain and a method for preparing a sulfide oxidase preparation from the same. This strain is a *Streptomyces* sp. strain DS021-$Z_5D_2$ which is a mutant having a high yield of sulfide oxidase obtained by taking a *Streptomyces* sp. strain DS021 as a starting strain and performing strain mutation by means of compound mutation of ultraviolet light and diethyl sulfate, and the preservation number is CGMCC No. 12808. This strain has the advantages of quick growth speed, high enzymatic productivity and the like. When this strain is fermented by a high-density fermentation method, this strain can produce sulfide oxidase preparations at a high yield. This strain has the advantages of inexpensive and easily-available culture substrates, high enzymatic productivity, short fermentation period, low production and use cost, and the like.

6 Claims, No Drawings

Specification includes a Sequence Listing.

STREPTOMYCES SP. STRAIN AND METHOD FOR PREPARING SULFIDE OXIDASE PREPARATION FROM THE SAME

CROSS-REFERENCE TO RELATED APPLICATION

This application claims the priority of Chinese Patent Application No. 201610739207.X, filed to the Chinese Patent Office on Aug. 26, 2016, titled "*STREPTOMYCES* SP. STRAIN AND METHOD FOR PREPARING SULFIDE OXIDASE PREPARATION FROM THE SAME", which is incorporated herein by reference in its entirety.

TECHNICAL FIELD

The present invention relates to a *Streptomyces* sp. strain and a method for preparing a sulfide oxidase preparation from the same, belonging to the field of biotechnology and bioengineering.

BACKGROUND OF THE PRESENT INVENTION

Due to the large population density of China and the rapid development of the industry, the environmental management and protection measures are not harmonized with the rapid industrialization, agriculture and the urbanized development, and the odor pollution resulted from sulfides is very serious. In the environment, odorous pollutant components from industrial production links and from decomposition of biological substances enter the atmosphere to form serious olfactory pollution, thereby damaging the human and animal nerves, decreasing the appetite, accelerating the amnesia, and retarding the blood circulation, all of which severely threaten the life. If such pollutant components are present in oil and gas, equipment and pipes will be corroded seriously. Some of such pollutant components may enter water along with waste water and wastes, and water smells malodorous. Consequently, the survival of aquatic organisms is affected directly, and the ecological cycle is destroyed. Malodorous substances are widely present in livestock farms, aquaculture farms, sewage treatment plants, chemical plants, refuse transfer stations, public toilets, domestic sewage and the like, and the malodorous smell has become a typically social public hazard.

Sulfide oxidase preparations, commonly known as deodorant enzyme preparations, are microbial enzyme preparations prepared from particular microbial spawns by the modern fermentation engineering under the appropriate conditions, and are a kind of biologically active macromolecules with the ability to degrade malodorous sulfides by oxidation-reduction reactions. Such products are modern biotechnological products which are non-toxic, harmless, safe and efficient, free of secondary environmental pollution in use, and biodegradable. The energy consumption in controlling malodorous smell by biological technologies and methods is low. The bio-oxidized malodorous substances can be assimilated by plants and microorganisms to form compositions of organisms, without any pollution. The biological treatment has mild conditions, high reaction efficiency and low operating cost. In view of its characteristics, the biological deodorization has become a hot topic in many countries, and has become a development direction of the management of malodorous substances. On Mar. 5, 2016, the thirteen Five-Year Plan Outline of the National Economic and Social Development of the People's Republic of China proposed to develop green and environmental protection industries and expand the supply of environmental protection products and services; and, in terms of industries, to develop and expand emerging industries, rebuild and upgrade traditional industries, and accelerate the construction of a new system of environmentally-friendly modern industries with high innovation capability. In view of the biological properties of sulfide oxidase, the products are environmentally-friendly products, and the production enterprises are green and environmental protection industries.

LUAN, Xingshe, the inventor of the present invention patent application, has developed a method for preparing a deodorant enzyme preparation by fermentation (invention patent: ZL200910015863.5). In this method, the deodorant enzyme preparation was prepared by optimally culturing the separated facultative autotrophic *Streptomyces* sp. strain DS-021 capable of generating a deodorant enzyme, and good effects have been realized. For the sulfide oxidase preparations which are environmentally-friendly biological preparations, under the premise of scientific and rational processes and efficient product applications, further improving the technical contents on the basis of the prior art, increasing the product yield, accordingly reducing the production and use cost are technical problems to be overcome and technical supports to be provided for the industrialization of the technology and the promotion and application of the products.

SUMMARY OF THE PRESENT INVENTION

To solve the above technical solutions, the present invention employs the following technical solutions.

One aspect of the present invention provides a *Streptomyces* sp. strain DS021-$Z_5D_2$, the preservation number of which is CGMCC No. 12808. This strain is a mutant having a high yield of sulfide oxidase obtained by taking a *Streptomyces* sp. strain DS021 as a starting strain and performing strain mutation by means of compound mutation of ultraviolet light and diethyl sulfate. This strain has been preserved in the China General Microbiological Culture Collection Center (CGMCC, address: Institute of Microbiology of Chinese Academy of Sciences, No. 3, Yard 1, Beichen Road West, Chaoyang District, Beijing, China) on Jul. 21, 2016, and the preservation number is CGMCC No. 12808.

Another aspect of the present invention provides an application of the *Streptomyces* sp. strain DS021-$Z_5D_2$ described in the above technical solution in preparing a sulfide oxidase preparation.

Still another aspect of the present invention provides a method for preparing a sulfide oxidase preparation from the *Streptomyces* sp. strain DS021-$Z_5D_2$ described in the above technical solution, including the following steps:

(1) Liquid Spawn Culture activated slant spawn is inoculated into a liquid spawn culture medium, and then cultured while shaking at 150-180 r/min at 25-40° C. for 30-46 h to obtain a liquid spawn for later use;

(2) High-Density Fermentation the liquid spawn is inoculated into a fermentation medium in a volume ratio of 3-6% and batch fermented for 15-19 h; and, then fed-batch fermented is performed, where the mass concentration of starch in a fermentation broth is controlled at 1.5-2.0% to perform the flow-plus culture; the fermentation time being total 45-58 h;

(3) the thallus is removed from the fermentation broth, and 3%-8% in mass of a protectant dextrin is added into the fermentation broth, to eventually obtain a liquid sulfide oxidase preparation;

The liquid spawn culture medium contains the following components in gram per liter (g/L): 10-15 g/L of starch, 1.5-3.0 g/L of $KNO_3$, 0.8-1.5 g/L of $K_2HPO_4$, 0.4-0.9 g/L of $MgSO_4$, 0.3-0.8 g/L of NaCl, 0.5-1.0 g/L of $CaCl_2$, 0.01-0.04 g/L of $FeSO_4$, 1.0-4.0 g/L of corn steep, and 18-38 g/L of bran;

The fermentation medium contains the following components in gram per liter (g/L): 20-40 g/L of starch, 2-5 g/L of $KNO_3$, 1-3 g/L of $K_2HPO_4$, 0.2-0.7 g/L of $MgSO_4$, 0.2-0.8 g/L of NaCl, 0.5-1.0 g/L of $CaCl_2$, 0.01-0.04 g/L of $FeSO_4$, 0.02-0.07 g/L of $MnSO_4$, 2-6 g/L of corn steep, and 20-40 g/L of bran.

The present invention has the following technical effects: in the present invention, an excellent *Streptomyces* sp. $DS021-Z_5D_2$ mutant strain is obtained by means of compound mutation of ultraviolet light and diethyl sulfate on the basis of an existing strain DS021; compared with the existing strain, this strain has the advantages of quick growth speed, high enzymatic productivity and the like. In the present invention, when this strain as a production strain is fermented by a high-density fermentation method, this strain can produce microbial sulfide oxidase at a high yield. This strain has the advantages of inexpensive and easily-available culture medium, high enzymatic productivity (enzymatic productivity≥2300 U/mL), short fermentation period (58 h), low production and use cost, and the like. The product is non-toxic, harmless, safe, efficient, environmentally-friendly, and biodegradable. When the microbial sulfide oxidase prepared in the present invention is applied to the deodorization of sewage containing sulfides, the degradation rate of sulfides is up to 98.05%. Such a microbial sulfide oxidase has board development prospect and high application value.

DETAILED DESCRIPTION OF THE PRESENT INVENTION

The screening of *Streptomyces* sp. strains, the method for preparing a sulfide oxidase preparation, and the use effects of the sulfide oxidase preparation will be described below in details by example embodiments, so that the advantages and characteristics of the present invention may be understood by those skilled in the art more easily, and the protection scope of the present invention is defined more clearly.

According to one aspect of the present invention, this embodiment provides a *Streptomyces* sp. strain $DS021-Z_5D_2$, the preservation number of which is CGMCC No. 12808. This strain is a mutant having a high yield of sulfide oxidase obtained by taking a *Streptomyces* sp. strain DS021 as a starting strain and performing strain mutation by means of compound mutation of ultraviolet light and diethyl sulfate. This strain has been preserved in the China General Microbiological Culture Collection Center (CGMCC, address: Institute of Microbiology of Chinese Academy of Sciences, No. 3, Yard 1, Beichen Road West, Chaoyang District, Beijing, China) on Jul. 21, 2016, and the preservation number is CGMCC No. 12808. After this strain is cultured for 7 d on a Czapek Dox agar medium, the colony diameter is 7.5 mm (the colony diameter of the starting strain DS021 is 4 mm); and, after this strain is cultured for 7 d on an Emerson agar medium, the colony diameter is 9.5 mm (the colony diameter of the DS021 is 5 mm). When this strain was dibbled onto an amylase-active plate and then cultured for 5 d, the diameter of a transparent circle/the colony diameter is 3.1 (the colony diameter of the DS021 is 2.2). Therefore, compared with the existing strain DS021, the strain provided by the present invention has the advantages of quick growth speed and high enzymatic productivity.

The culture medium for the common preservation of this strain is Goates No. 1 synthetic agar, which specifically has the following components: 2% of soluble starch, 0.1% of $KNO_3$, 0.05% of $K_2HPO_4$, 0.05% of NaCl, 0.05% of $MgSO_4.7H_2O$, 0.001% of $FeSO_4.7H_2O$, and 1.5% of agar powder. The pH is 7.2 to 7.4.

According to another aspect of the present invention, this embodiment provides a method for preparing a sulfide oxidase preparation from the *Streptomyces* sp. strain $DS021-Z_5D_2$ described in the above embodiment, including the following steps:

(1) Liquid Spawn Culture

Activated slant spawn is inoculated into a liquid spawn culture medium, and then cultured while shaking at 150-180 r/min at 25-40° C. for 30-46 h to obtain a liquid spawn for later use.

In this step, to obtain the desired liquid spawn, it is required to control the culture temperature, the time and the shaking condition after the activated slant spawn is inoculated into the liquid spawn culture medium. In a preferred embodiment, the culture temperature may be 25° C., 28° C., 30° C., 32° C., 35° C., 38° C., 40° C. or the like, the culture time may be 32 h, 34 h, 36 h, 38 h, 40 h, 42 h, 44 h or 46 h, and the shaking condition may be 150 r/min, 160 r/min, 170 r/min, 180 r/min or the like. The culture temperature, the culture time and the shaking condition are not specifically limited in this embodiment, and may be selected within the above reasonable scopes as required by those skilled in the art.

(2) High-Density Fermentation

The liquid spawn is inoculated into a fermentation medium in a volume ratio of 3-6% and batch fermented for 15-19 h; and, then fed-batch fermented is performed, where the mass concentration of starch in a fermentation broth is controlled at 1.5-2.0% to perform the flow-plus culture; the fermentation time is total 45-58 h.

In this step, the effects of the high-density fermentation are realized by characteristic fed-batch fermentation according to the cell growth condition, the state of fermentation substrates and other characteristics. The fermentation time is total 45-58 h during which the time for the batch fermentation is 15-19 h. By measuring the fermentation broth, the dry weight of mycelia is greater than or equal to 1.63 g/100 mL (the dry weight of mycelia is used as a measure for the growth of the spawn), and the enzymatic activity of the sulfide oxidase is greater than or equal to 2300 U/mL.

(3) The thallus is removed from the fermentation broth, and 3%-8% in mass of a protectant dextrin is added into the fermentation broth, to eventually obtain a liquid sulfide oxidase preparation.

The liquid spawn culture medium contains: 10-15 g/L of starch, 1.5-3.0 g/L of $KNO_3$, 0.8-1.5 g/L of $K_2HPO_4$, 0.4-0.9 g/L of $MgSO_4$, 0.3-0.8 g/L of NaCl, 0.5-1.0 g/L of $CaCl_2$, 0.01-0.04 g/L of $FeSO_4$, 1.0-4.0 g/L of corn steep, and 18-38 g/L of bran. The fermentation medium contains: 20-40 g/L of starch, 2-5 g/L of $KNO_3$, 1-3 g/L of $K_2HPO_4$, 0.2-0.7 g/L of $MgSO_4$, 0.2-0.8 g/L of NaCl, 0.5-1.0 g/L of $CaCl_2$, 0.01-0.04 g/L of $FeSO_4$, 0.02-0.07 g/L of $MnSO_4$, 2-6 g/L of corn steep, and 20-40 g/L of bran.

In a preferred embodiment, the fermentation conditions in the step (2) are controlled as follows: fermentation temperature: 28-38° C.; air volume/culture volume/min: 0.25-0.8 VVM; and stirring speed: 200-600 r/min. It should be understood that the fermentation conditions are preferred fermentation conditions, where the fermentation temperature may also be 28° C., 30° C., 32° C., 34° C., 36° C., 38° C. or the like; the air volume/culture volume/min may also be 0.3 VVM, 0.4 VVM, 0.5 VVM, 0.6 VVM, 0.7 VVM or 0.8 VVM; and, the stirring speed may be 250 r/min, 300 r/min, 350 r/min, 400 r/min, 450 r/min, 500 r/min or 550 r/min. The fermentation conditions are not specifically limited in this embodiment, and may be selected within the above reasonable scopes as required by those skilled in the art. It is to be noted that the fermentation conditions described in this embodiment are fermentation conditions for the batch fermentation and the fed-batch fermentation.

In a preferred embodiment, a fed-batch liquor for the fed-batch fermentation is an aqueous solution of starch and potassium nitrate in a mass ratio of 15-18:1. Specifically, the mass ratio of starch to potassium nitrate may be 15:1, 16:1, 17:1 or 18:1. A method for preparing the fed-batch liquor for the fed-batch fermentation is as follows: starch and potassium nitrate are dissolved in water at the mass ratio described above, then heated and gelatinized with vapor while stirring, sterilized for 25 min at 0.1 Mpa, and cooled to 30° C. for later use, where the solid content in the fed-batch liquor is generally 6%±1%.

This embodiment further provides a usage of the sulfide oxidase prepared by the preparation method described above: the sulfide oxidase in a liquid state is directly mixed into sewage or dirt containing malodorous sulfides. The usage amount is designed in such a way that the volume of enzyme (i.e., the amount of active units) is determined according to the content of sulfides in the sewage or dirt, and 1 U of enzyme needs to be added in order to degrade 1 μg of $S^{2-}$ in 1 h.

In order to describe the present invention in more details, the present invention will be described below by specific embodiments.

With regard to the active unit of enzyme, the volume of enzyme required for oxidizing 1 μg of $S^{2-}$ in 1 h at 35° C. and 170 r/min, by taking 0.1 mg/mL of $S^{2-}$ solution as a substrate, is defined as 1 active unit of enzyme, expressed by U/mL (U/g). $S^{2-}$ is measured by methylene blue.

Embodiment 1

(1) Induced Mutation and Screening of Strain
① Culture Medium and Fabrication Thereof
Slant culture medium (g/L): 20 g/L of soluble starch, 1 g/L of $KNO_3$, 0.5 g/L of $K_2HPO_4$, 0.5 g/L of NaCl, 0.5 g/L of $MgSO_4.7H_2O$, 0.01 g/L of $FeSO_4.7H_2O$, and 15 g/L of agar powder, where the pH is 7.2 to 7.4.

$Na_2S$-resistant culture medium (g/L): 20 g/L of soluble starch, 1.2 g/L of $KNO_3$, 1.5 g/L of $K_2HPO_4$, 0.6 g/L of NaCl, 0.7 g/L of $MgSO_4.7H_2O$, 0.015 g/L of $FeSO_4.7H_2O$, 0.015 g/L of $K_2Cl_2O_7$, 8 g/L of $Na_2S.9H_2O$, and 15 g/L of agar powder.

Fabrication of a $Na_2S$-resistant gradient plate: a culture dish having a diameter of 9 mm was prepared; 8 mL of dissolved slant culture medium was poured into the culture dish to serve as an underlying layer, and the plate was placed obliquely; after the slant culture medium is solidified, 8 mL of dissolved $Na_2S$-resistant culture medium was poured into the culture dish to serve as an overlying layer, and the plate was placed horizontally; and after the $Na_2S$-resistant culture medium is solidified, a $Na_2S$-resistant gradient plate is eventually obtained.

② Preparation of a monospore suspension of a starting strain: the slant spawn that had been cultured for 7 d was added with 10 mL of sterile water to wash off spores, then poured into a 50 mL triangular flask containing glass beads, shaken fully to disperse cenobium, and filtered with a sterile qualitative filter paper to eventually obtain the monospore suspension.

③ Irradiation by ultraviolet light (UV): 5 mL of the monospore suspension was added into a culture dish having a diameter of 9 cm, and then irradiated for 90 s at a distance of 30 cm by a UV lamp of 30 W while stirring by a magnetic stirrer, to eventually obtain a UV-induced spore suspension.

④ Dilution and coating of the plate: in the presence of red light, the UV-induced spore suspension was serially diluted, 0.2 mL of the diluted spore suspension having a dilution degree of $10^{-4}$ to $10^{-6}$ was coated onto the $Na_2S$-resistant gradient plate and then cultured for 2-5 day at 28° C. away from light. Strains having high $Na_2S$-resistance and quick growth speed were numbered and then preserved on a slant to eventually obtain the UV-induced strains.

⑤ Induced mutation by diethyl sulfate (DES): the UV-induced strain slant was added with sterile water by the method described above to eventually obtain a monospore suspension. 15 mL of a phosphate buffer solution and 5 mL of the monospore suspension were added into a 250 mL triangular flask, then added with 0.5% of DES, and reacted for 30 min at 35° C. and at 160 r/min while shaking; and the reaction system was added with 1 mL of 25% sodium thiosulfate to stop the reaction. Subsequently, the system was serially diluted, 0.2 mL of the diluent having a dilution degree of $10^{-4}$ to $10^{-6}$ was coated onto the $Na_2S$-resistant gradient plate, and then cultured for 2-5 day at 28° C. DES-induced colonies having quick growth were numbered and preserved on a slant to eventually obtain a strain $DS021$-$Z_5D_2$ induced by both the UV and the DES.

(2) Identification of Strain
This strain had the following culture characteristics: this strain has substrate mycelia and aerial mycelia; the aerial mycelia form straight or waved spore hyphae in the later stage of growth, and the spore hyphae differentiate into a large amount of spores when they are matured. The substrate mycelia secrete soluble pigments. The secreted pigments are different in colors, depending upon the grown different culture mediums. For example, the pigments were apricot on a Goates No. 1 synthetic medium, yellowish gray on a Czapek's medium, and bright orange yellow on the Emerson agar. The color of the aerial mycelia and the color of the spore hyphae are gull gray on the potato extract agar, and cocoon white on the Emerson agar. This strain has a quick growth speed. After this strain is cultured for 7 d on a Czapek Dox agar medium, the colony diameter is 7.5 mm (the colony diameter of the starting strain DS021 is 4 mm). This strain has the most growth speed on the Emerson agar. After this strain is cultured for 7 d on the Emerson agar, the colony diameter is 9.5 mm (the colony diameter of the DS021 is 5 mm).

This strain has the following physiological and biochemical characteristics: the anabolism of amylase is vigorous; when this strain is dibbled onto an amylase-active plate and then cultured for 5 d, the diameter of a transparent circle/the colony diameter is 3.1 (the DS021 is 2.2); the milk coagulation and peptonization capability is high; this strain can grow using cellulose; and, this strain does not result in hydrogen sulfide. The starch, arabinose and xylose are the optimal carbon sources, the yeast extract is the optimal organic nitrogen, and potassium nitrate and ammonium bicarbonate are the optimal inorganic nitrogen.

The following is the measurement result of the 16SrDNA sequence of this train (SEQ-1):

```
ACGCTGGCGGCGTGCTTAACACATGCAAGTCGAACGATGAACCACTT
CGGTGGGGATTAGTGGCGAACGGGGGAGTAACACGTGGGCAATCTGCCCT
GCACTCTGGGACAAGCCCTGGAAACGGGGTCTAATACCGGATACTGACCC
GCTTGGGCATCCAAGCGGTTCGAAAGCTCCGGCGGTGCAGGATGAGCCCG
CGGCCTATCAGCTTGTTGGTGAGGTAATGGCTCACCAAGGCGACGACGGG
TAGCCGGCCTGAGAGGGCGACCGGCCACACTGGGACTGAGACACGGCCCA
GACTCCTACGGGAGGCAGCAGTGGGGAATATTGCACAATGGGCGAAAGCC
TGATGCAGCGACGCCGCGTGAGGGATGACGGCCTTCGGGTTGTAAACCTC
TTTCAGCAGGGAAGAAGCGAAAGTGACGGTACCTGCAGAAGAAGCGCCGG
CTAACTACGTGCCAGCAGCCGCGGTAATACGTAGGGCGCGAGCGTTGTCC
GGAATTATTGGGCGTAAAGAGCTCGTAGGCGGCTTGTCACGTCGGTTGTG
AAAGCCCGGGGCTTAACCCCGGGTCTGCAGTCGATACGGGCAGGCTAGAG
TTCGGTAGGGGAGATCGGAATTCCTGGTGTAGCGGTGAAATGCGCAGATA
TCAGGAGGAACACCGGTGGCGAAGGCGGATCTCTGGGCCGATACTGACGC
TGAGGAGCGAAAGCGTGGGGAGCGAACAGGATTAGATACCCTGGTAGTCC
ACGCCGTAAACGGTGGGCACTAGGTGTGGGCGACATTCCACGTCGTCCGT
GCCGCAGCTAACGCATTAAGTGCCCCGCCTGGGGAGTACGGCCGCAAGGC
TAAAACTCAAAGGAATTGACGGGGGCCCGCACAAGCGGCGGAGCATGTGG
CTTAATTCGACGCAACGCGAAGAACCTTACCAAGGCTTGACATACACCGG
AAACGTCCAGAGATGGGCGCCCCCTTGTGGTCGGTGTACAGGTGGTGCAT
GGCTGTCGTCAGCTCGTGTCGTGAGATGTTGGGTTAAGTCCCGCAACGAG
CGCAACCCTTGTCCCGTGTTGCCAGCAAGCCCTTCGGGGTGTTGGGGACT
CACGGGAGACCGCCGGGGTCAACTCGGAGGAAGGTGGGGACGACGTCAAG
TCATCATGCCCCTTATGTCTTGGGCTGCACACGTGCTACAATGGCCGGTA
CAATGAGCTGCGATACCGCGAGGTGGAGCGAATCTCAAAAAGCCGGTCTC
AGTTCGGATTGGGGTCTGCAACTCGACCCCATGAAGTCGGAGTCGCTAGT
AATCGCAGATCAGCATTGCTGCGGTGAATACGTTCCCGGGCCTTGTACAC
ACCGCCCGTCACGTCACGAAAGTCGGTAACACCCGAAGCCGGTGGCCCAA
CCCCTTGTGGGAGGGAGCTGTCGAAGGTGG.
```

This strain has been preserved in the China General Microbiological Culture Collection Center (CG MCC, address: Institute of Microbiology of Chinese Academy of Sciences, No. 3, Yard 1, Beichen Road West, Chaoyang District, Beijing, China) on Jul. 21, 2016, and the preservation number is CGMCC No. 12808.

Embodiment 2

(1) Liquid Spawn Culture

Activated slant spawn was inoculated into a liquid spawn culture medium, and then cultured while shaking at 180 r/min at 35° C. for 38 h to obtain a liquid spawn for later use.

The liquid spawn culture medium contains the following components in gram per liter (g/L):12 g/L of starch, 2.5 g/L of $KNO_3$, 1.5 g/L of $K_2HPO_4$, 0.6 g/L of $MgSO_4$, 0.5 g/L of NaCl, 0.7 g/L of $CaCl_2$, 0.015 g/L of $FeSO_4$, 2.5 g/L of corn steep, and 28 g/L of bran.

(2) High-Density Fermentation

The fermentation medium contains the following components in gram per liter (g/L): 37 g/L of starch, 2.5 g/L of $KNO_3$, 1.6 g/L of $K_2HPO_4$, 0.6 g/L of $MgSO_4$, 0.4 g/L of NaCl, 0.6 g/L of $CaCl_2$, 0.01 g/L of $FeSO_4$, 0.025 g/L of $MnSO_4$, 3 g/L of corn steep, and 30 g/L of bran.

A fed-batch liquor for fed-batch fermentation was prepared as follows: 56.5 g of starch and 3.5 g of potassium nitrate were dissolved in 1000 mL of water, then heated and gelatinized with vapor while stirring, sterilized for 25 min at 0.1 Mpa, and cooled to 30° C. for later use.

The liquid spawn was inoculated into the fermentation medium in an inoculation amount (in volume) of 3.5%, and then batch fermented for 18 h. Subsequently, fed-batch fermentation was performed, where the mass concentration of starch in a fermentation broth was controlled at 1.5-2.0% to perform the flow-plus culture. The fermentation conditions were controlled as follows: temperature: 35° C.; air volume/culture volume/min: 0.35 VVM; stirring speed: 550 r/min; and the total fermentation time: 52 h.

By measuring the fermentation broth, the dry weight of mycelia was 1.69 g/100 mL, and the enzymatic activity of sulfide oxidase was 2385 U/mL.

In contrast, a fermentation broth was obtained by taking a strain DS021 as spawn and by the method described in Embodiment 1 of ZL200910015863.5, where the dry weight of mycelia was 0.87 g/100 mL, and the enzymatic activity of sulfide oxidase was 1250 U/mL.

As can be seen, the dry weight of mycelia and the enzyme production efficiency in the present invention are improved by 94.3% and 90.8% respectively compared with the original starting strain DS021, and the improvement effects are significant.

(3) The thallus was removed from the fermentation broth, and 5% in mass of a protectant dextrin was added into the fermentation broth, to eventually obtain a liquid sulfide oxidase preparation.

Embodiment 3

The liquid spawn culture medium, the fermentation medium and the fed-batch liquor are the same as those in Embodiment 2. Differences between this embodiment and Embodiment 2 lie in the following aspects.

(1) Liquid Spawn Culture

Activated slant spawn was inoculated into a liquid spawn culture medium, and then cultured while shaking at 160 r/min at 32° C. for 40 h to obtain a liquid spawn for later use.

(2) High-Density Fermentation

The liquid spawn was inoculated into the fermentation medium in an inoculation amount (in volume) of 3.8%, and then batch fermented for 19 h. Subsequently, fed-batch fermentation was performed, where the mass concentration of starch in a fermentation broth was controlled at 1.5-2.0% to perform the flow-plus culture. The fermentation conditions were controlled as follows: temperature: 32° C.; air volume/culture volume/min: 0.40 VVM; stirring speed: 500 r/min; and the total fermentation time: 54 h.

The dry weight of mycelia was greater than or equal to 1.63 g/100 mL, and the enzymatic activity of sulfide oxidase was greater than or equal to 2300 U/mL.

(3) The thallus was removed from the fermentation broth, and 4.5% in mass of a protectant dextrin was added into the fermentation broth, to eventually obtain a liquid sulfide oxidase preparation.

Embodiment 4

The liquid spawn culture medium, the fermentation medium and the fed-batch liquor are the same as those in Embodiment 2. Differences between this embodiment and Embodiment 2 lie in the following aspects.
(1) Liquid Spawn Culture
Activated slant spawn was inoculated into a liquid spawn culture medium, and then cultured while shaking at 170 r/min at 36° C. for 39 h to obtain a liquid spawn for later use.
(2) High-Density Fermentation
The liquid spawn was inoculated into the fermentation medium in an inoculation amount (in volume) of 3.6%, and then batch fermented for 18 h. Subsequently, fed-batch fermentation was performed, where the mass concentration of starch in a fermentation broth was controlled at 1.5-2.0% to perform the flow-plus culture. The fermentation conditions were controlled as follows: temperature: 36° C.; air volume/culture volume/min: 0.32 VVM; stirring speed: 500 r/min; and the total fermentation time: 50 h.

The dry weight of mycelia was greater than or equal to 1.63 g/100 mL, and the enzymatic activity of sulfide oxidase was greater than or equal to 2300 U/mL.
(3) The thallus was removed from the fermentation broth, and 4.8% in mass of a protectant dextrin was added into the fermentation broth, to eventually obtain a liquid sulfide oxidase preparation.

Embodiment 5

Treatment of Sewage Containing Malodorous Sulfides
The microbial sulfide oxidase preparations prepared in Embodiments 2-4 were applied to the treatment of raw water containing malodorous sulfides (the sulfide content was 966 mg/L) in an absorption tower, where the usage amount of the sulfide oxidase is designed in such a way that 20000 U/L of the raw water reacted for 1 h at 35° C.; and, the results of enzymatic oxidation was that the sulfide degradation loads in per liter of raw water was about 947.2 mg and the degradation rate of sulfides was up to 98.5%. As can be seen, the microbial sulfide oxidase preparations prepared in the embodiments of the present invention may be efficiently applied to the deodorization of sewage containing sulfides, the degradation rate of sulfides is up to 98.05%. Such microbial sulfide oxidase preparations have board development prospect and high application value.

The invention claimed is:

1. A *Streptomyces* sp. strain DS021-Z$_5$D$_2$, the preservation number of which is CGMCC No. 12808.

2. A method of preparing sulfide oxidase by culturing the microorganism *Streptomyces* sp. strain DS021-Z$_5$D$_2$ of claim 1 under appropriate culture conditions and obtaining a sulfide oxidase preparation.

3. A method for preparing a sulfide oxidase preparation from the *Streptomyces* sp. strain DS021-Z$_5$D$_2$ of claim 1, comprising the following steps:

(1) liquid spawn culture activated slant spawn is inoculated into a liquid spawn culture medium, and then cultured while shaking at 150-180 r/min at 25-40° C. for 30-46 h to obtain a liquid spawn for later use;

(2) high-density fermentation the liquid spawn is inoculated into a fermentation medium in a volume ratio of 3-6% and batch fermented for 15-19 h; and, then fed-batch fermented is performed, where the mass concentration of starch in a fermentation broth is controlled at 1.5-2.0% to perform the flow—plus culture; the fermentation time being total 45-58 h;

(3) the thallus is removed from the fermentation broth, and 3%-8% in mass of a protectant dextrin is added into the fermentation broth to eventually obtain a liquid sulfide oxidase preparation;

the liquid spawn culture medium is: 10-15 g/L of starch, 1.5-3.0 g/L of KNO$_3$, 0.8-1.5 g/L of K$_2$HPO$_4$, 0.4-0.9 g/L of MgSO$_4$, 0.3-0.8 g/L of NaCl, 0.5-1.0 g/L of CaCl$_2$, 0.01-0.04 g/L of FeSO$_4$, 1.0-4.0 g/L of corn steep, and 18-38 g/L of bran; and the fermentation medium is: 20-40 g/L of starch, 2-5 g/L of KNO$_3$, 1-3 g/L of K$_2$HPO$_4$, 0.2-0.7 g/L of MgSO$_4$, 0.2-0.8 g/L of NaCl, 0.5-1.0 g/L of CaCl$_2$, 0.01-0.04 g/L of FeSO$_4$, 0.02-0.07 g/L of MnSO$_4$, 2-6 g/L of corn steep, and 20-40 g/L of bran; and obtaining the sulfide oxidase preparation.

4. The method for preparing a sulfide oxidase preparation according to claim 3, wherein the fermentation conditions in the step (2) are as follows: fermentation temperature: 28-38° C.; air volume/culture volume/min: 0.25-0.8 VVM; and stirring speed: 200-600 r/min.

5. The method for preparing a sulfide oxidase preparation according to claim 3, wherein a fed-batch liquor for the fed-batch fermentation is an aqueous solution of starch and potassium nitrate in a mass ratio of 15-18:1.

6. The method for preparing a sulfide oxidase preparation according to claim 5, wherein the solid content of the fed-batch liquor is 6%±1%.

* * * * *

SEQUENCE LISTING

```
<160> NUMBER OF SEQ ID NOS: 1

<210> SEQ ID NO 1
<211> LENGTH: 1427
<212> TYPE: DNA
<213> ORGANISM: Streptomyces sp.

<400> SEQUENCE: 1
acgctggcgg cgtgcttaac acatgcaagt cgaacgatga accacttcgg tggggattag      60
tggcgaacgg gggagtaaca cgtgggcaat ctgccctgca ctctgggaca agccctggaa     120
acggggtcta ataccggata ctgacccgct tgggcatcca agcggttcga aagctccggc     180
ggtgcaggat gagcccgcgg cctatcagct tgttggtgag gtaatggctc accaaggcga     240
cgacgggtag ccggcctgag agggcgaccg gccacactgg gactgagaca cggcccagac     300
tcctacggga ggcagcagtg gggaatattg cacaatgggc gaaagcctga tgcagcgacg     360
ccgcgtgagg gatgacggcc ttcgggttgt aaacctcttt cagcagggaa gaagcgaaag     420
tgacggtacc tgcagaagaa gcgccggcta actacgtgcc agcagccgcg gtaatacgta     480
gggcgcgagc gttgtccgga attattgggc gtaaagagct cgtaggcggc ttgtcacgtc     540
ggttgtgaaa gcccggggct taacccggg tctgcagtcg atacgggcag gctagagttc     600
ggtaggggag atcggaattc ctggtgtagc ggtgaaatgc gcagatatca ggaggaacac     660
cggtggcgaa ggcggatctc tgggccgata ctgacgctga ggagcgaaag cgtggggagc     720
gaacaggatt agataccctg gtagtccacg ccgtaaacgg tgggcactag gtgtgggcga     780
cattccacgt cgtccgtgcc gcagctaacg cattaagtgc cccgcctggg gagtacggcc     840
gcaaggctaa aactcaaagg aattgacggg ggcccgcaca agcggcggag catgtggctt     900
aattcgacgc aacgcgaaga accttaccaa ggcttgacat acaccggaaa cgtccagaga     960 tgggcgccc cttgtggtcg gtgtacaggt ggtgcatggc tgtcgtcagc tcgtgtcgtg    1020
agatgttggg ttaagtcccg caacgagcgc aacccttgtc ccgtgttgcc agcaagccct    1080
```

```
tcggggtgtt   ggggactcac   gggagaccgc   cggggtcaac   tcggaggaag   gtggggacga    1140
cgtcaagtca   tcatgcccct   tatgtcttgg   gctgcacacg   tgctacaatg   gccggtacaa    1200
tgagctgcga   taccgcgagg   tggagcgaat   ctcaaaaagc   cggtctcagt   tcggattggg    1260
gtctgcaact   cgacccatg    aagtcggagt   cgctagtaat   cgcagatcag   cattgctgcg    1320
gtgaatacgt   tcccgggcct   tgtacacacc   gcccgtcacg   tcacgaaagt   cggtaacacc    1380
cgaagccggt   ggcccaaccc   cttgtgggag   ggagctgtcg   aaggtgg                   1427
```